United States Patent [19]

Barrickman

[11] 4,438,768
[45] Mar. 27, 1984

[54] EMERGENCY CRICOTHYROIDOTOMY INSTRUMENT

[76] Inventor: Robert W. Barrickman, R.D. #2, Box 139C, Clarion, Pa. 16214

[21] Appl. No.: 304,807

[22] Filed: Sep. 23, 1981

[51] Int. Cl.³ .................... A61F 17/32; A61M 15/08
[52] U.S. Cl. .............................. 128/305.3; 128/207.14
[58] Field of Search ............. 128/305.3, 343, 329 R, 128/330, 200.26, 207.14, 207.16, 207.17, DIG. 26; 604/117, 272; 30/316, 130, 294; 269/237, 270

[56] References Cited

U.S. PATENT DOCUMENTS

| | | | |
|---|---|---|---|
| 447,776 | 3/1891 | Islin | 269/237 |
| 2,674,966 | 4/1954 | Morris | 269/237 |
| 2,923,299 | 2/1960 | Blackwood | 128/351 |
| 3,137,299 | 6/1964 | Tabor | 128/207.16 |
| 3,202,023 | 8/1965 | Parker | 269/270 |
| 3,307,551 | 3/1967 | Violet, Jr. | 128/305 |
| 3,415,250 | 12/1968 | Peterson | 128/305 |
| 3,688,773 | 9/1972 | Weiss | 128/329 |
| 3,760,811 | 9/1973 | Andrew | 128/207.17 |
| 3,760,811 | 9/1973 | Andrew | 128/351 |
| 3,916,903 | 11/1975 | Pozzi | 128/305.3 |
| 4,235,229 | 11/1980 | Ranford et al. | 128/207.17 |
| 4,291,690 | 9/1981 | Jessen | 128/200.26 |
| 4,304,228 | 12/1981 | Depel | 128/207.17 |
| 4,332,245 | 6/1982 | Boone, Sr. | 128/207.14 |

Primary Examiner—Richard J. Apley
Assistant Examiner—Harry J. Macey
Attorney, Agent, or Firm—Webb, Burden, Robinson & Webb

[57] ABSTRACT

A cricothyroidotomy instrument having an elongated needle and a holder for the needle. The needle has a sharp point on one end, a flange on the other end and a longitudinal passage extending from the end of the needle with the sharp point to the end of the needle with the flange. The needle holder has two separable sections having faces which abut when the needle holder is closed and spaced annular grooves are formed in the abutting faces. A plurality of annular spaced beads is formed on the exterior surface of the needle which engage the annular grooves in the needle holder. A latch maintains the separable sections in the closed relationship to clamp the needle in the needle holder.

11 Claims, 3 Drawing Figures

U.S. Patent  Mar. 27, 1984  4,438,768
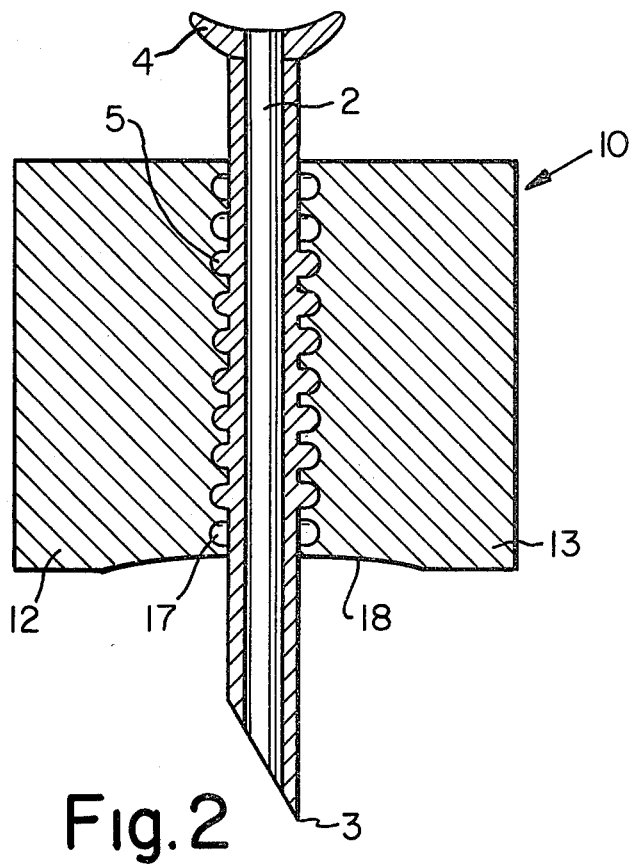
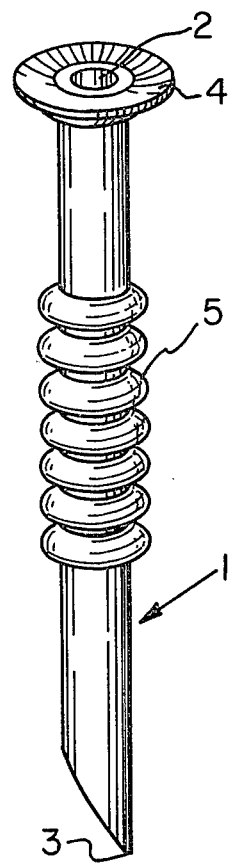
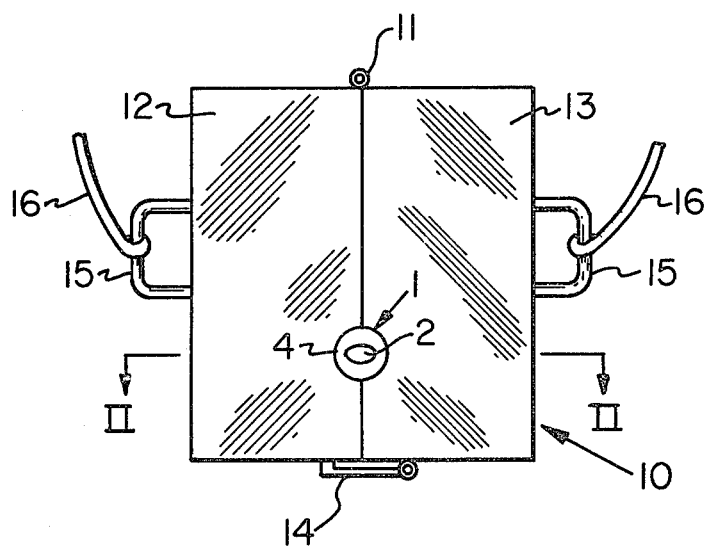

EMERGENCY CRICOTHYROIDOTOMY INSTRUMENT

BACKGROUND OF THE INVENTION

1. Field of the Invention

This invention relates to an instrument for performing an emergency cricothyroidotomy to prevent a person from choking to death when a foreign object is lodged in the throat or when severe trauma occurs.

2. Description of the Prior Art

Choking is a relatively frequent cause of death which occurs when a piece of food or foreign matter lodges in the throat causing suffocation. Trauma can also cause blockage of the throat in which case breathing will be severely limited or stopped. In the past when a person is choking, removal of the object lodged in the throat has been effected by a hard slap on the back, physically pulling out the object with the fingers or by the Heimlich maneuver which requires a person to stand behind the person who is choking and wrap their arms around the victim's abdomen just below the ribs and with a quick, hard jerk, force the air from the victim's lungs which will, hopefully, eject the object which is lodged in the throat. However, these procedures are not always successful in which case a person can die from suffocation caused by choking.

In hospitals and in out-patient care centers a tracheotomy may be performed by trained medical personnel to create an airway to the trachea when a person is choking. However, tracheotomies per se are not designed to be performed away from hospitals or similar environments.

A need exists for a simple lifesaving instrument for victims who fail to respond to a slap on the back or to the Heimlich maneuver and who are not in the immediate proximity of a hospital where a tracheotomy can be performed. Military and civilian medical personnel are taught to perform emergency cricothyroidotomy by using available instruments as a pen knife, a fountain pen, a pencil or even a small stick with a pointed end to form an airway until a tracheotomy can be performed or the object is surgically or manually removed. In this procedure a hole is punched in the trachea through the skin below the cricothyroid artery in the cricothyroid cartilage area. This hole allows the victim to breathe until the foreign object is removed from the throat or until the trauma situation no longer exists.

SUMMARY OF THE INVENTION

An instrument consisting of a hollow metal needle with a flange at one end and a sharp point at the other end. A plurality of annular external beads are located around the middle portion of the needle. A metal or plastic needle holder surrounds the needle and clamps it to hold it in place after it has been inserted. Rounded indentations are formed in the needle holder which correspond in size and location to the beads on the exterior of the needle so that the needle is secured in the needle holder. The needle holder has a strap or elastic band which fits around the neck and prevents the needle from slipping out of position. The inner surface of the needle holder is shaped to comfortably embrace the throat area of a patient.

BRIEF DESCRIPTION OF THE DRAWINGS

FIG. 1 is an elevation of the needle holder with a needle clamped therein;

FIG. 2 is a section on line II—II of FIG. 1; and

FIG. 3 is an elevation of a needle.

DESCRIPTION OF THE PREFERRED EMBODIMENTS

The needle 1 will vary in size for a child and for an adult size. The needle has an air passage 2 which extends longitudinally throughout the length of the needle from the end with a sharpened point 3 to the end formed with a flange 4. The diameter of passage 2 will vary from about 1.5 millimeters to approximately 4.0 millimeters, and the overall length of the needle will vary from approximately 25 millimeters to 50 millimeters. The passage through the needle may be either oval in cross section as shown in FIGS. 1 and 2 or cylindrical in cross section as shown in FIG. 3, and it will be understood by those skilled in the art that a passage with an oval cross section will permit a greater amount of air to pass through the needle. A plurality of individual spaced annular beads 5 is formed on the exterior surface of the needle in an area approximately equal spaced between point 3 and flange 4. These individual beads cooperate with the needle holder in the manner shown in FIG. 2 of the drawings to hold the needle in position at the proper depth in a person's trachea. Adjustment of the depth of penetration of the needle in the trachea may be required according to the size and muscle structure of the patient, and such adjustment is made possible by providing the needle with beads 5 in a manner explained hereinafter.

Point 3 of needle 1 must be extremely sharp in order to permit easy puncture and penetration through the skin, cartilage and other tissues into the trachea. Flange 4 is approximately 10 millimeters in diameter and prevents needle 1 from fully penetrating the skin and/or trachea and serves as a thumb rest to insert needle 1 into the trachea. Additionally, flange 4 permits a resuscitating air bag or a human mouth to be placed on the outer end of needle 1 to force air through passage 2 into the trachea, if such is necessary.

A needle holder 10 may be made of either plastic or metal and has an elongated hinge 11 at one end to permit sections 12 and 13 to be pivotally separated so that the needle holder may be clamped around a needle after it is inserted in the trachea. A mechanical catch or latch 14 is formed on the end of the needle holder opposite the end carrying hinge 11 to clamp sections 12 and 13 in position around a needle after the needle holder is placed on the needle and sections 12 and 13 are closed. A magnetic catch may also be used to hold sections 12 and 13 in the closed position. The needle holder is provided with flanges or hasps 15 on the side faces of the needle holder, and a pair of straps 16 or a unitary elastic band is attached to hasps 15. When the needle holder is in position, straps 16 are tied behind the patient's neck or the elastic band is fitted around the back of the patient's neck to hold the needle holder in position. The abutting surfaces of sections 12 and 13 are formed with a plurality of annular grooves 17 which receive beads 5 on the exterior surface of the needle. As will be seen in FIG. 2 of the drawings, beads 5 and annular grooves 17 are equally spaced the same distance apart in order to permit the position of the needle to be adjusted when the needle holder is placed around the needle. If necessary, one or more beads 5 may be located outside of needle holder 10. The lower surface of the needle holder is formed with a contoured area 18 to embrace a patient's neck.

The needle holder will be about one to two inches in length depending upon whether it is adult size or child size and the width will be between one inch and two inches. The needle holder will be about three quarters of an inch thick.

In operations the instrument is inserted through the patient's skin into the trachea. The needle will pass through the cricothyroid cartilage and into the trachea but should not be forced in so far as to go completely through the trachea. After the needle is inserted, the patient can breathe normally through the passage in the needle or by forced breathing, if necessary. Once the needle is satisfactorily placed in the trachea, the needle holder is placed around the needle and clamped securely to the needle. The needle holder is then fastened around the patient's neck with either an elastic band or ties, and the patient may then be transported to a hospital without fear of suffocation.

Suffocation from choking in the home or in a restaurant may be prevented by performing an emergency cricothyroidotomy with the instrument of the invention. Choking caused by trauma from vehicular and other accidents may also be avoided by using the instrument by police and emergency medical personnel. The instrument may be used on numerous occasions by military personnel, emergency medical technicians, hospital emergency room personnel and by industrial and school nurses.

While preferred embodiments of the invention have been described herein, it is to be understood that they may be embodied within the scope of the appended claims.

I claim:

1. A cricothyroidotomy instrument comprising an elongated unitary needle and a needle holder, said needle having a sharp point on one end and a longitudinal passage extending from the end of said needle with said sharp point to the opposite end of said needle, means on a portion of the exterior surface of said needle adapted to engage said needle holder, said needle holder having separable sections, each of said sections having a face adapted to abut a face of the other section, means on the abutting faces of said separable sections adapted to contact said means on the exterior surface of said needle to hold said needle in said needle holder, means to retain said separable sections in a closed relationship with said abutting faces in contact to clamp said needle in said needle holder, and means on said needle holder adapted to attach said needle holder to a patient's neck.

2. Apparatus as set forth in claim 1 wherein said needle includes a flange on the end opposite the pointed end.

3. Apparatus as set forth in claim 1 or 2 wherein said means on the exterior surface of said needle is a plurality of spaced annular beads.

4. Apparatus as set forth in claim 1 wherein said means on the exterior surface of said needle is a plurality of longitudinally spaced annular beads and said means on the abutting faces of said separable sections of said needle holder are spaced annular grooves, the spacing of said grooves being the same as the spacing of said annular beads on the exterior surface of said needle.

5. Apparatus as set forth in claim 1 wherein said separable sections are connected by a hinge for pivotal movement of said sections to open and close said needle holder, whereby said needle holder can be placed around said needle with said separable sections in an open position and can be pivoted to the closed position.

6. Apparatus as set forth in claim 1 wherein said means to retain said separable sections in the closed relationship is a pivoted latch.

7. Apparatus as set forth in claim 1 wherein said longitudinal passage has a circular cross section.

8. Apparatus as set forth in claim 1 wherein said longitudinal passage has a generally oval shaped cross section.

9. A unitary needle for use in a cricothyroidotomy instrument, said needle having an elongated body with a longitudinal passage extending completely therethrough, a sharp point on one end of said needle, a flange on the end of said needle opposite said one end with said sharp point and a plurality of spaced annular beads on the exterior surface of said needle adapted to be held by a needle holder.

10. A needle as set forth in claim 9 wherein said longitudinal passage has a circular cross section.

11. A needle as set forth in claim 9 wherein said longitudinal passage has a generally oval shaped cross section.

* * * * *